(12) United States Patent
Rosengaus

(10) Patent No.: US 7,280,197 B1
(45) Date of Patent: Oct. 9, 2007

(54) WAFER EDGE INSPECTION APPARATUS

(75) Inventor: Eliezer Rosengaus, Palo Alto, CA (US)

(73) Assignee: KLA-Tehcor Technologies Corporation, San Jose, CA (US)

(*) Notice: Subject to any disclaimer, the term of this patent is extended or adjusted under 35 U.S.C. 154(b) by 301 days.

(21) Appl. No.: 10/992,419

(22) Filed: Nov. 17, 2004

Related U.S. Application Data

(60) Provisional application No. 60/591,797, filed on Jul. 27, 2004.

(51) Int. Cl.
*G01N 22/88* (2006.01)

(52) U.S. Cl. .................. 356/237.1; 356/237.2

(58) Field of Classification Search ............ 356/237.1, 356/237.2, 237.3, 237.4, 237.5; 382/145, 382/149; 257/E21.53
See application file for complete search history.

(56) References Cited

U.S. PATENT DOCUMENTS

| | | | |
|---|---|---|---|
| 6,798,503 B2 | 9/2004 | Hiramoto et al. | 356/237.5 |
| 2003/0169916 A1 | 9/2003 | Hayashi | 382/145 |
| 2004/0239920 A1* | 12/2004 | Kreh et al. | 356/237.3 |
| 2005/0024632 A1* | 2/2005 | Plemmons et al. | 356/237.1 |
| 2005/0280807 A1* | 12/2005 | Backhauss et al. | 356/237.2 |

* cited by examiner

*Primary Examiner*—Richard A. Rosenberger
(74) *Attorney, Agent, or Firm*—Deborah Wenocur

(57) ABSTRACT

A wafer edge inspection system utilizes a novel camera and mirror arrangement which conveys the images of the various near-edge wafer regions in piecewise fashion to a linear sensor array on a single line-scan sensor. This system is low-cost and compact, and may be integrated into various wafer handling or processing machines or systems.

33 Claims, 4 Drawing Sheets

WAFER EDGE INSPECTION APPARATUS

CROSS-REFERENCE TO RELATED APPLICATIONS

This application claims priority from U.S. Provisional Application No. 60/591,797, filed Jul. 27, 2004.

FIELD OF THE INVENTION

This invention relates to semiconductor wafer inspection for integrated circuit processing, and in particular to a compact, cost-effective apparatus for inspecting wafer edge regions.

BACKGROUND OF THE INVENTION

A critical step in integrated circuit processing is defect detection, which has multiple components. One of these components is the inspection and detection of defects at or near the wafer edge. Wafer edges can develop a number of types of defects during processing, which include but are not limited to: chips, cracks, and contamination such as resist residue. Edge defect sizes of interest may range from 1-2 microns for contamination, up to 100-500 microns or more for edge chips. These edge defects do not directly impact yield by affecting IC operation, however they can be the underlying cause of catastrophic failures. For example, if a wafer edge is chipped or cracked, subsequent exposure to high-temperature processing steps such as Rapid Thermal Processing (RTP) or Chemical Vapor Deposition (CVD) can cause the wafer to shatter. This can result in, not only the loss of that particular wafer, but contamination of the other wafers in the process chamber, as well as contamination of the equipment, which is costly and time-consuming to clean up. Thus, effective edge inspection and defect detection can have great importance in optimizing yield and throughput of wafers.

Since the edge defects do not directly cause yield loss, as described above, the calculation for Return on Investment (ROI) for edge inspection systems is complicated. Edge defects may be infrequent, thus requiring 100% inspection of each wafer in order to detect process control problems. Therefore, a high-throughput, low-cost edge inspection system is required in order to provide a favorable ROI.

FIG. 1 illustrates and defines the wafer regions in the edge vicinity, for a 300 mm diameter wafer. Frontside 100 and backside 110 of wafer 120 include Fixed Quality Area (FQA) 125, Edge Exclusion (EE) region 127 of width 2-3 mm, including top near edge region 130 and bottom near edge region 140, top bevel 150, and bottom bevel 160, each encompassing about 0.5 mm radial dimension. Apex 170 has a vertical dimension of about 0.5 mm. Note that the illustration shows an ideal profile: actual wafer profiles in the edge vicinity may be a continuous curve or have rounded corners, rather than having distinct planar bevel and apex regions as shown.

Several edge inspection systems are currently being marketed, for example by Raytex, Honda Electron, and EVG. The Raytex system is described in U.S. Pat. No. 6,798,503, issued Sep. 28, 2004. The Honda Electron system is described is US Patent Application Publication No. US2003/0169916 μl, published on Sep. 11, 2003. In general, these available systems utilize multiple sensors and/or cameras at different positions to inspect the top (130) and bottom (140) wafer surfaces as well as the bevel (150, 160) and apex (170) regions. By way of example, Honda Electron and EVG use multiple cameras positioned to separately image the top (130), bottom (140), and bevel (150,160) regions. Another system, manufactured by Raytex, uses a laser source directed at the wafer apex, and an elliptical mirror where the apex is at a first focus, and scattered light is collected at the second focus. The scattering flags potentially defective areas, which are then imaged by additional cameras to reject false positives and nuisance-type defects. For example, small contaminating particles may not be of interest to a customer, but may scatter sufficient light to trigger the laser scattering apparatus. These "nuisance" defects need to be identified and filtered out so as not to overwhelm the user with a large number of them.

The use of multiple cameras yields bulky inspection systems and also increases the system cost. It also requires multiple high-speed interfaces to capture the acquired images into computer memory, which also increases the cost of multiple cameras.

An edge inspection system providing simultaneous inspection of multiple edge vicinity regions selected from: top 130 and bottom 140 near-edge, apex 170, and bevel 150, 160 regions, projected in piecewise fashion onto a linear sensor array, preferably with a single camera in a compact head, would be highly advantageous, both in reducing cost, and in enabling integration to a front-end wafer handler.

SUMMARY OF THE INVENTION

It is therefore an object of this invention to provide an improved apparatus for wafer edge inspection which can utilize a single camera.

It is a further object of this invention to provide an improved apparatus for wafer edge inspection which can be sufficiently compact to be integrated into a front-end wafer handler.

It is a further object of this invention to provide an improved apparatus for wafer edge inspection which is low-cost.

These objects are met by providing a camera and mirror arrangement which conveys the images of the various near-edge wafer regions in piecewise fashion to a linear sensor array on a single line-scan sensor.

DETAILED DESCRIPTION OF THE INVENTION

The inventive apparatus is constructed to convey images of several regions of interest onto a linear sensor array of a high pixel-count line scan camera. The image of the portion of the wafer near the edge, including the curved bevel/apex region, is mapped onto the linear sensor array in multiple sections via multiple optical paths. This configuration helps to correct for the problem of non-uniform sensitivity which occurs when imaging a curved surface in two dimensions: when using a line sensor, sensitivity is uniform in at least one dimension. Another advantage of using line-scan cameras is that this ensures that every line is captured in the same illuminator-line-camera geometry. Since the wafers are highly reflective, this allows the geometry to be set to prevent specular reflections or "glints", which could saturate the sensors, making them locally blind to defects. The preferred embodiments of the invention utilize a single line scan camera, although a plurality of cameras may be utilized for some applications.

Figure 1:
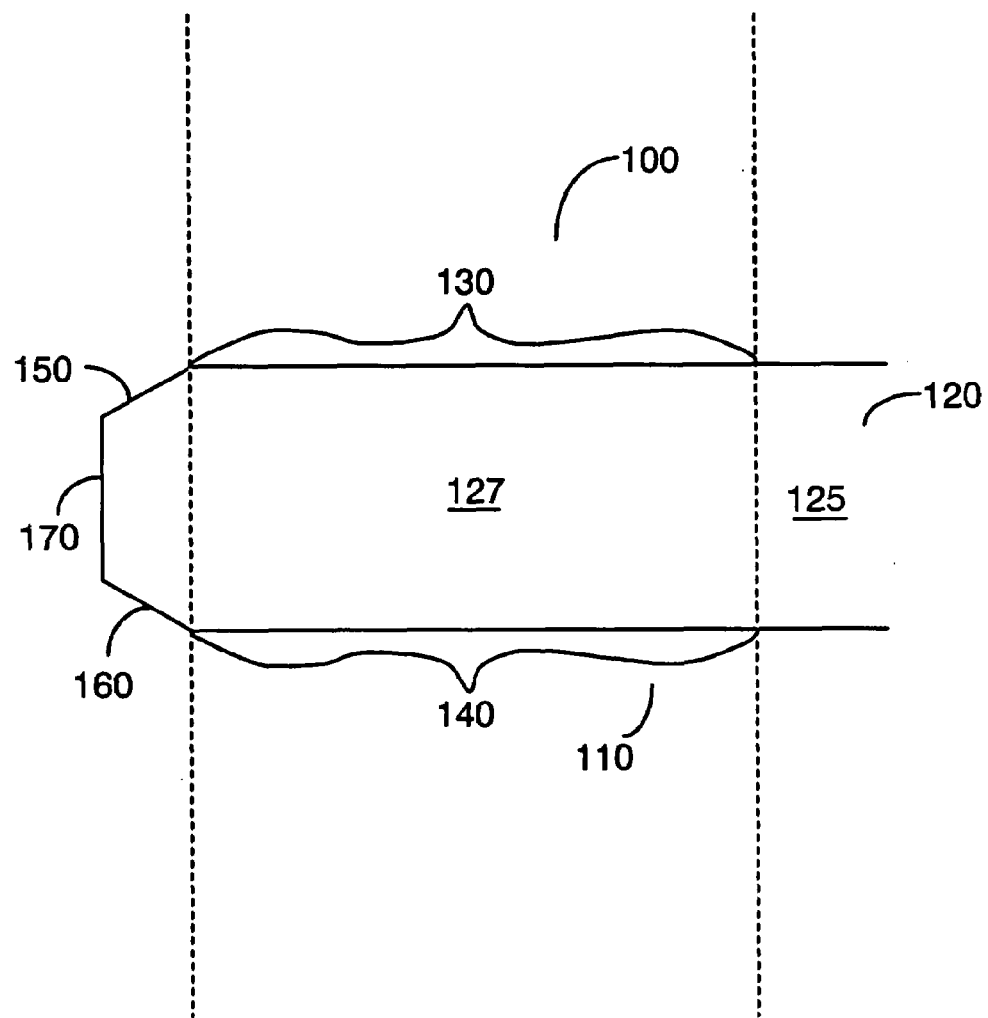
FIG. 1 illustrates the near-edge regions of a wafer.
Figure 2A:
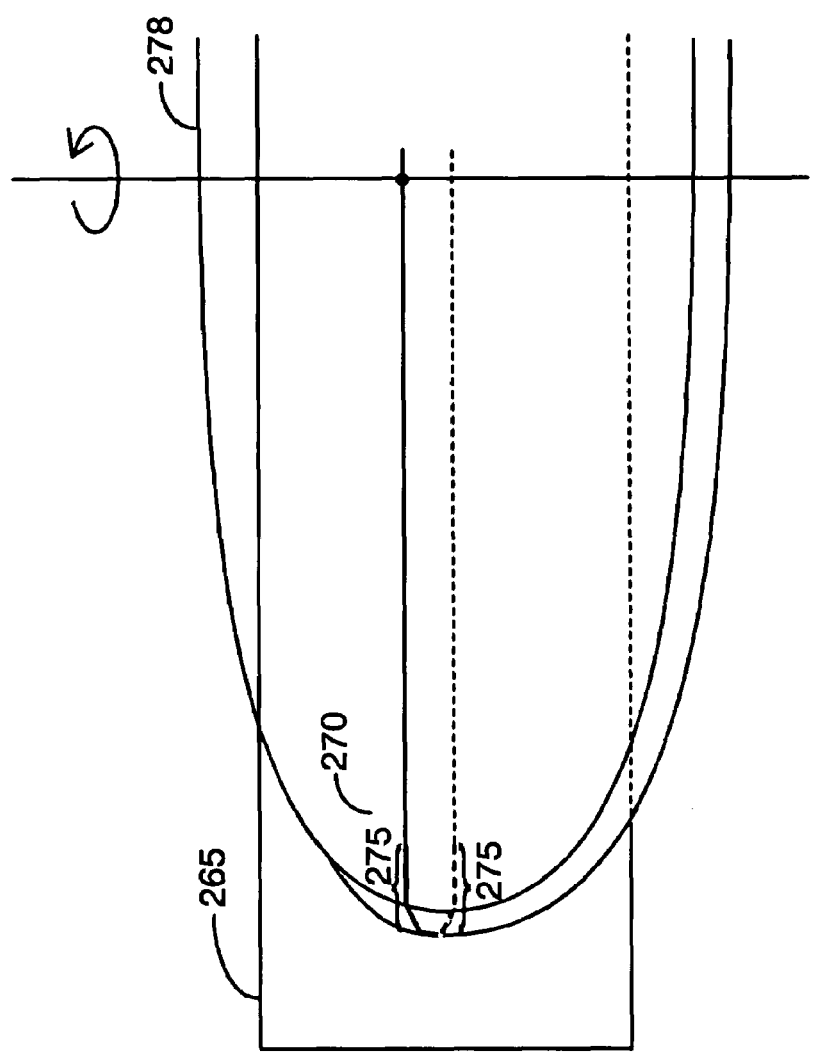
FIG. 2a (not drawn to scale) illustrates the portion of the wafer being imaged at an instant of time.

FIG. 2a illustrates the region of the wafer being imaged at an instant in time according to a first preferred sub-embodiment of the present invention: the intersection of plane 265 with near-edge wafer surface 270. The image from this curve 275 is mapped in a piecewise fashion, providing a piecewise flat projection onto the linear sensor array, by an inventive mirror arrangement described hereinafter, to provide a line of data. As the wafer is rotated around axis 278 (generally by being spun on a chuck), the camera images around the edge of the wafer and digitizes the lines of data; the lines of data are transferred to computer memory, wherein an image of the wafer edge region is built. Software processes the different regions of interest to detect deviations from uniformity (which denote defects), and retains high resolution image clips for review and classification. These images may be displayed as desired.

High pixel count line-scan cameras are commercially available from different vendors. By way of example, DALSA sells an 8000 pixel Piranha-2 camera with high-speed readout at 40 million pixels/second. This permits reading 5000 lines of input per second. For a 300 mm wafer with a circumference of about 1 meter, and using 5 micron wide samples for a total of 200,000 samples per edge, inspection would take 40 seconds per wafer. DALSA also makes camera units with up to 160 million pixels per second readout. It should be noted that a wide range of pixel counts and readout speeds may be utilized, with the throughput varying as a result.

300 mm wafers are about 750 microns thick. The near-edge regions of interest include about the outer 3 mm radially. Thus, the total "length" of the line to be inspected in this first embodiment, as illustrated in FIG. 2a, (i.e., top near-edge 130+bottom near-edge 140+apex+bevel) is about 6750 microns. At 1 micron pixel width, 6750 pixels would be required. In reality, 1 micron pixels would yield prohibitively long inspection times, so 2-5 micron pixel widths are more likely.

Alternate preferred sub-embodiments of the invention inspect a subset of the edge vicinity regions of the wafer, although also in piecewise fashion using multiple optical paths. By way of example, just the top near-edge region 130, top bevel region 150, and apex region 170 may be imaged using a single camera.

Figure 2B:
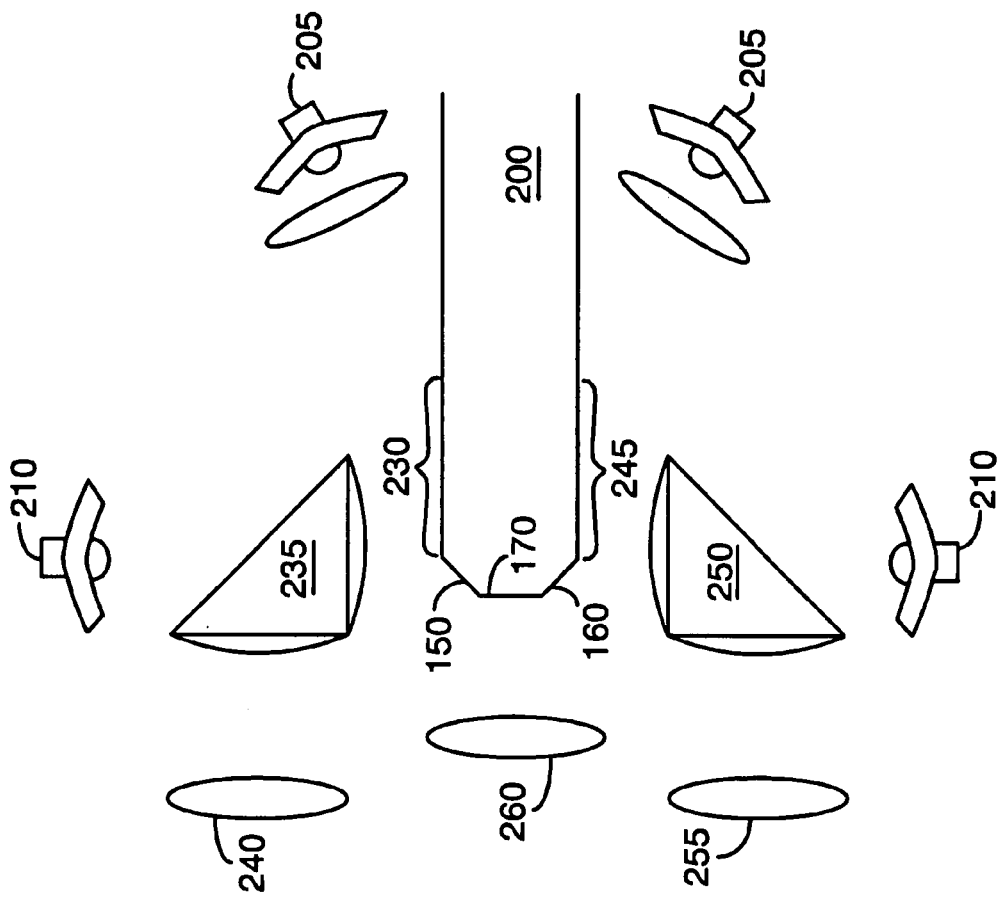
FIG. 2b illustrates the illumination and detection configuration of the inventive apparatus.
Figure 2B:
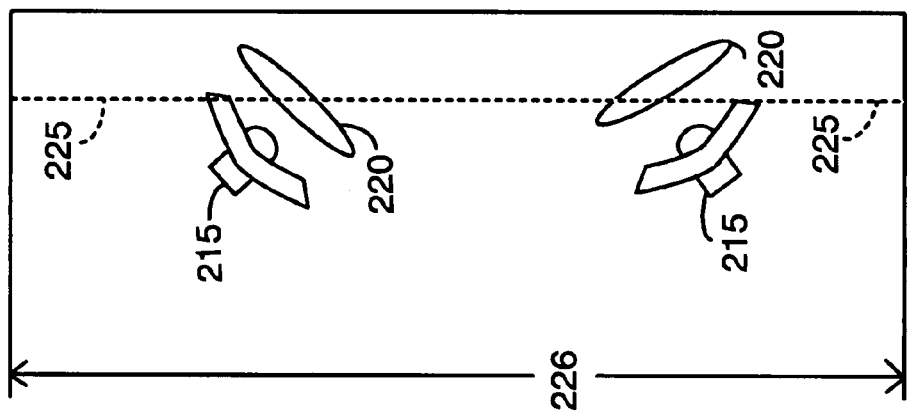

FIG. 2b illustrates the configuration of the inventive apparatus for the first preferred embodiment of the invention. Wafer 200, oriented in a plane defined herein as being the horizontal xy plane, is illuminated by several illuminators directed at different regions of the wafer. The illuminators may be direct illuminators (such as light bulbs), LED's, fiber-optic delivery systems, and/or lasers, depending on the defects of interest. Top and bottom near edge illuminators 205 provide incoming light at an angle for dark field illumination, i.e., scattered light is collected. Bright field illumination can be provided by illuminators 210, wherein reflected light is collected, which is useful for classifying defects located by the dark field illumination. Apex illuminators 215 illuminate the bevel and apex regions from a direction out of the plane of the figure. This is because the apex region exhibits high curvature (750 micron curvature diameter) in the thickness dimension, defined herein as being the vertical dimension. The effectively high curvature of the edge region exists whether the edges are beveled or filleted, though it is continuous in the second case and discontinuous in the first case.

Since the wafer is polished, a highly curved surface, whether beveled or filleted as described above, will produce a specular reflection or "glint" for any illumination angle if the illuminators are in the plane of the sensor. These glints produce a blind spot in those areas by saturating the sensors. The problem is eliminated by moving the illuminators out of the plane of the sensor, since curvature in the plane of the wafer is comparatively small (300 mm diameter). Illuminator lenses 220 focus the illumination onto the regions of interest.

Three separate optical paths image the regions of interest onto single line-scan sensor 225 which is oriented vertically, i.e., perpendicular to the plane of the wafer, and having the sensor surface centers directly facing the apex surface. The camera's dimensions include the height 226 of the sensor scan line, which will be defined as being in the z-direction; the camera is centered relative to the wafer in the z-direction. The sensor array directly faces the apex surface; i.e., the camera faces radially relative to wafer 200.

The reflected or scattered light from top near-edge region 230 is redirected onto sensor 225 via reflecting element 235, which may be a 45-degree prism as shown, or may be a mirror or beam splitter. Alternatively, a refractive element or fiber optic array may be used. Lensing system 240 provides imaging and controls magnification. Reflected or scattered light from bottom near-edge region 245 is redirected onto sensor 225 via reflecting element 250 and lensing system 255. Reflected or scattered light from apex 170 and bevel 150, 160 regions is redirected onto sensor 225 via lensing system 260. The lenses are chosen to focus the images of the regions of interest onto the sensor line.

The alternate preferred sub-embodiments outlined above may also utilize a subset of the apparatus described for the first embodiment.

A second embodiment of the invention employs a plurality of cameras, while maintaining the inventive method of piecewise projection of the curved surface near the wafer edge onto a flat linear scanner array. This alternate embodiment may be utilized for applications which do not have size restraints.

A first advantage of the preferred embodiment of the inventive system is its relatively low cost, since it utilizes only a single camera and a single computer interface, compared with currently available multi-camera systems.

A second advantage of the preferred embodiment of the inventive apparatus is its monolithic character, wherein there is no problem of registration between multiple cameras, in contrast to the currently available systems. As a result, the lenses can be mounted rigidly, thereby avoiding vibration problems.

A third advantage of the inventive system and method is that, using the piecewise projection as described, the camera does not need to have a large depth of focus (DOF). Large DOF limits the numerical aperture (NA) of the camera, and reduces the ability to collect sufficient light, therefore requiring much brighter illumination or longer imaging times and lower throughput.

A fourth, important advantage of the preferred embodiment of the inventive apparatus over the commercially available systems is its compactness. A compact system such as the one described herein has the capability of being integrated into various wafer handling or processing machines or systems. For example, Front Opening Unified Pods (FOUPS, SEMI Standard E47.1), i.e. the boxes containing wafers which are used to transfer wafers between systems while maintaining a controlled environment, have very limited internal space. Another example is the typical interface between the clean room and the processing equipment, which may include the opener for opening the FOUP box, known as Front-Opening Interface Mechanical Standard (FIMS, SEMI Standard E62-0302). This interface generally contains a pre-aligner which translates and rotates the wafer into proper position before loading, as well as robotic arms to load and unload wafers. As in the FOUP box, space is generally quite confined.

The inventive edge inspection system is compact enough to mount inside either the FOUP box or onto the pre-aligner of most front-end handlers, as opposed to the currently available multi-camera inspection systems. If mounted on a pre-aligner, the inventive compact system can be moved closer to the wafer following pre-alignment of the wafer, and this allows the use of smaller, less costly lenses. Alternately, additional optical components can be added to increase the separation of the prisms from the wafer surface, to facilitate wafer loading or unloading while still focusing all three images onto the sensor line.

Figure 3:
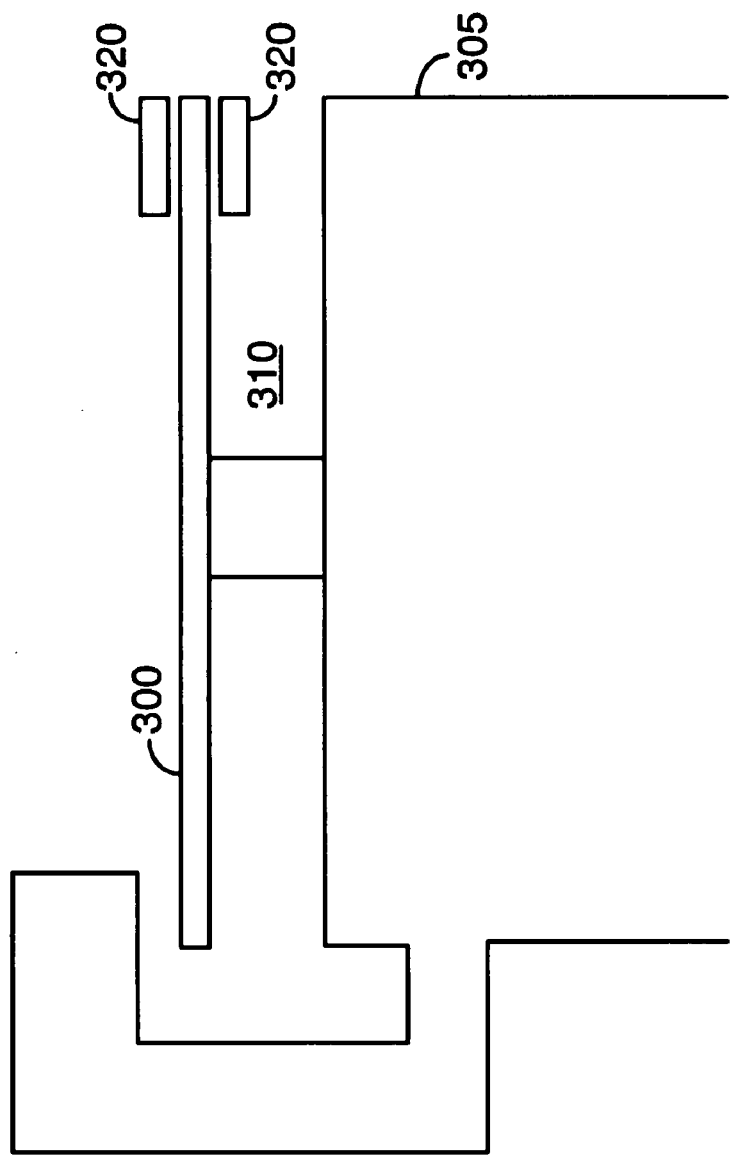
FIG. 3 illustrates a modified pre-aligner configuration to increase wafer stability.

When using the edge inspection system on a pre-aligner 305, a center-supported pre-aligner avoids the complication of edge-handling clips of an edge-handling pre-aligner, which could interfere with inspection. The configuration of a typical center-supported pre-aligner 305 is illustrated in FIG. 3. Wafer 300 is supported in the center only by support 310, generally held by vacuum suction. As the wafer is rotated, its edges can bow downwards and also flop up and down. If an edge inspection system is mounted on the pre-aligner, this instability can cause problems, particularly with depth-of-focus. A solution is to add air bearings 320 near the wafer edges to stabilize the edges of the wafer. An edge- handling pre-aligner could be accommodated using a retractable camera that skips over the edge handling clips; the wafer would then be re-grabbed with a different angular orientation and the spots skipped over in the first pass could then be inspected.

Due to its compactness, the inventive edge inspection system can be utilized as an Integrated inspection System, i.e., it can be integrated with other systems or machines, and can be portable if mounted in FOUP boxes. It therefore provides the capability of having multiple wafer edge inspections on various pieces of processing equipment to localize problems.

The present invention provides a compact, low-cost, high-throughput, preferably single-camera wafer edge-inspection system which can be integrated into front-end wafer handlers. It is not intended that the invention be restricted to the exact embodiments described herein. Modifications can be made without departing from the inventive concept. For example, the exact types of illuminators and optical components can be modified. For another example, the top and bottom edge illuminators may additionally illuminate all or a part of the bevel regions, and the bevel regions may be partially imaged through the same optical paths as the edge regions. For another example, the invention is not limited to 300 mm wafers, and is applicable to 200 mm wafers or other wafer sizes. The inspection system may be mounted elsewhere other than on the pre-aligner of a wafer handler. The scope of the invention should be construed in view of the claims.

With this in mind, I claim:

1. A wafer edge inspection apparatus configured to be mounted proximal the edge region of a wafer, said wafer being oriented in an xy plane, said edge region including a first edge subregion comprising a top edge surface; a second edge subregion comprising a bottom edge surface; a third edge subregion comprising a top bevel surface; a fourth edge subregion comprising a bottom bevel surface; and a fifth edge subregion comprising an apex surface, said apparatus comprising:

at least one illumination source positioned to illuminate a portion of each of a plurality of said edge subregions of said wafer;

at least one camera, said camera including a linear sensor array on a single line-scan sensor, said linear sensor array having a center, said linear sensor array being oriented substantially perpendicular to said xy plane of said wafer in the z-direction, said linear sensor array having sensor surfaces with their centers substantially normal to a first radial line including the center of said wafer and said linear sensor array;

at least one optical element positioned to direct a piecewise projected image of said portion of each of a plurality of said edge subregions of said wafer onto said single line-scan sensor of said camera, said image including multiple image sections, each said image section being directed through a separate optical path to said single line-scan sensor of said camera; and a computer connected to said camera configured to form an image of said plurality of edge subregions of said wafer.

2. The wafer edge inspection apparatus of claim 1, wherein said at least one camera is exactly one camera.

3. The wafer edge inspection apparatus of claim 2, wherein said at least one illumination source comprises a plurality of illuminators chosen from the group consisting of: a top edge illuminator positioned to illuminate a portion of said top edge surface of said wafer; a bottom edge illuminator positioned to illuminate a portion of said bottom edge surface of said wafer; and an apex illuminator positioned to illuminate a portion of said top bevel surface, said bottom bevel surface, and said apex surface of said wafer.

4. The wafer edge inspection apparatus of claim 2, wherein said at least one illumination source comprises:

at least one top edge illuminator positioned to illuminate a portion of said top edge surface of said wafer;

at least one bottom edge illuminator positioned to illuminate a portion of said bottom edge surface of said wafer; and at least one apex illuminator positioned to illuminate a portion of said top bevel surface, said bottom bevel surface, and said apex surface of said wafer.

5. The apparatus of claim 4, wherein:

said at least one top edge illuminator comprises: at least one top edge dark field illuminator, and at least one top edge bright field illuminator; and said at least one bottom edge illuminator comprises: at least one bottom edge dark field illuminator, and at least one bottom edge bright field illuminator.

6. The wafer edge inspection apparatus of claim 5, wherein said at least one optical element positioned to direct a piecewise projected image of said portion of each of a plurality of said edge subregions of said wafer onto said single line-scan sensor of said camera comprises:

a top optical element positioned to direct reflected and scattered light from said top edge surface of said wafer onto said single line-scan sensor;

a bottom optical element positioned to direct reflected and scattered light from said bottom edge surface of said wafer onto said single line-scan sensor; and wherein incident light on said top edge surface is provided by said top edge bright field illuminator and said top edge dark field illuminator, incident light on said bottom edge surface is provided by said bottom edge bright field illuminator and said bottom edge dark field illuminator, said incident light onto said top edge surface is reflected and scattered into said top optical element, and said incident light onto said bottom edge surface is reflected and scattered into said bottom optical element.

7. The apparatus of claim 4, wherein said at least one apex illuminator illuminates said apex from out of the plane defined by said linear sensor array and said first radial line including the center of said wafer and said linear sensor array.

8. The apparatus of claim 7, wherein said at least one apex illuminator comprises a top apex illuminator and a bottom apex illuminator.

9. The apparatus of claim 4, wherein each said at least one apex illuminator includes an illumination lens to focus the illumination onto a region of interest of said apex.

10. The apparatus of claim 4, wherein said illuminators are selected from the group consisting of: direct illuminators, LED's, fiber-optic delivery systems, and lasers.

11. The wafer edge inspection apparatus of claim 2, wherein said at least one optical element positioned to direct a piecewise projected image of said portion of each of a plurality of said edge subregions of said wafer onto said single line-scan sensor of said camera is selected from the group consisting of: lenses, reflecting elements, prisms, mirrors, beam splitters, refractive elements, and fiber optic arrays.

12. The wafer edge inspection apparatus of claim 11, wherein said at least one optical element positioned to direct a piecewise projected image of said portion of each of a plurality of said edge subregions of said wafer onto said single line-scan sensor of said camera comprises a plurality of optical elements chosen from the group consisting of:

at least one top optical element positioned to direct reflected and scattered light from said top edge surface of said wafer onto said single line-scan sensor; at least one bottom optical element positioned to direct reflected and scattered light from said bottom edge surface of said wafer onto said single line-scan sensor; and at least one apex optical element positioned to direct reflected and scattered light from said apex and bevel regions onto said single line-scan sensor.

13. The wafer edge inspection apparatus of claim 12, wherein:

said at least one top optical element is a reflecting element;

said at least one bottom optical element is a reflecting element; and said at least one apex optical element is a lens.

14. The wafer edge inspection apparatus of claim 13, further including a top lensing system positioned between said top reflecting element and said single line-scan sensor for focusing light from said top reflecting element onto said single line-scan sensor, and further including a bottom lensing system positioned between said bottom reflecting element and said single line-scan sensor for focusing light from said bottom reflecting element onto said single line-scan sensor.

15. The wafer edge inspection system apparatus of claim 13, wherein said top reflecting element and said bottom reflecting element are 45 degree prisms.

16. The wafer edge inspection apparatus of claim 2, further including a rotatable chuck for mounting of said wafer thereon.

17. The wafer edge inspection apparatus of claim 2, wherein said camera is a high pixel count line-scan camera.

18. The wafer edge inspection system apparatus of claim 17, wherein said camera has a high speed readout.

19. The wafer edge inspection system apparatus of claim 18, wherein said camera has a pixel count of at least 8000, and wherein said camera has a readout of at least 40 million pixels per second.

20. A wafer pre-aligner for translating and rotating a wafer into proper position before loading said wafer into processing equipment, said wafer aligner having the wafer edge inspection system of claim 1 mounted thereon, said wafer edge inspection system being positioned to inspect the edge region of said wafer.

21. The wafer pre-aligner of claim 20, wherein:

said wafer pre-aligner is edge-handling; and wherein said wafer edge inspection system includes a retractable camera.

22. The wafer pre-aligner of claim 20, including:

a support for center-supporting said wafer.

23. The wafer pre-aligner of claim 22, wherein said wafer is held onto said support by vacuum suction.

24. The wafer pre-aligner of claim 23, further including air bearings positioned near the edges of said wafer, above and below said wafer, proximal but not touching said wafer, for stabilizing said wafer edges during rotating of said wafer.

25. A Front-Opening Unified Pod (FOUP) box having the wafer edge inspection system of claim 2 mounted therein for edge inspection of wafers in said FOUP box.

26. A method for inspecting the edge region of a wafer, said wafer being oriented in an xy plane, said edge region including a first edge subregion comprising a top edge surface; a second edge subregion comprising a bottom edge surface; a third edge subregion comprising a top bevel surface; a fourth edge subregion comprising a bottom bevel surface; and a fifth edge subregion comprising an apex surface, comprising the steps of:

a) illuminating a portion of each of a plurality of said edge subregions of said wafer with at least one illumination source;

b) directing a piecewise projection image of said portion of each of a plurality of said edge subregions of said wafer onto a single line-scan sensor of at least one camera via at least one optical element, said image including multiple image sections, each said image section being directed through a separate optical path to said single line-scan sensor of said at least one camera, said at least one camera including a linear sensor array on a single line-scan sensor, said linear sensor array having a center, said linear sensor array being oriented substantially perpendicular to said xy plane of said wafer in the z-direction, said linear sensor array having sensor surfaces with their centers substantially normal to a first radial line including the center of said wafer and said linear sensor array;

c) repeating steps a) and b) with a series of different portions of said each of a plurality of said edge subregions to include the entire said plurality of said edge subregions of said wafer;

d) forming an image of said plurality of said edge subregions of said wafer using a computer connected to said at least one camera; and e) using said image of said plurality of said edge subregions of said wafer for one selected from the group consisting of: 1) affecting process control, and 2) disposition of said wafer to avoid catastrophic failures.

27. The method of claim 26, wherein said at least one camera is exactly one camera.

28. The method of claim 27, wherein:

said illuminators are selected from the group consisting of: direct illuminators, LED's, fiber-optic delivery systems, and lasers, and said optical elements are selected from the group consisting of: lenses, reflecting elements, prisms, mirrors, beam splitters refractive elements, and fiber optic arrays.

29. The method of claim 27, wherein said step of forming an image of said plurality of said edge subregions of said wafer comprises:

forming a digitized line of data from each image of a portion of each of a plurality of said edge subregions of said wafer directed onto said single line-scan sensor of said camera using said computer;

transferring each said digitized line of data to computer memory; and building an image of said plurality of said edge subregions of said wafer from said digitized lines of data.

30. The method of claim 26, wherein said step c) of repeating steps a) and b) with a series of different portions of each of a plurality of said edge subregions to include the entire said plurality of said edge subregions of said wafer comprises rotating said wafer around its central axis.

31. The method of claim 30, wherein said step of rotating said wafer around its central axis comprises spinning said wafer on a chuck.

32. The method of claim 26, further comprising, after step d) and prior to step e), the step of processing said image of said plurality of said edge subregions of said wafer to detect deviations from uniformity.

33. The method of claim 26, further comprising the step of retaining high resolution image clips for review and classification.

* * * * *